United States Patent [19]

Chen et al.

[11] Patent Number: 4,850,225
[45] Date of Patent: Jul. 25, 1989

[54] MEASURING VIBRATIONAL FREQUENCY OF VIBRATABLE PINS

[75] Inventors: Wayne G. Chen, West Palm Beach; Newman K. Lin, Boca Raton, both of Fla.

[73] Assignee: Northern Telecom Limited, Montreal, Canada

[21] Appl. No.: 264,368

[22] Filed: Oct. 31, 1988

[51] Int. Cl.[4] ............................................. G01N 29/00
[52] U.S. Cl. ......................................... 73/572; 73/588; 73/657; 356/349
[58] Field of Search ................. 73/572, 657, 648, 582, 73/588; 356/349, 355, 356, 357

[56] References Cited

U.S. PATENT DOCUMENTS

| | | | |
|---|---|---|---|
| 3,645,129 | 2/1972 | Grant | 73/582 |
| 4,287,766 | 9/1981 | Ensminger | 73/582 |
| 4,295,375 | 10/1981 | Ganglbauer et al. | 73/582 |
| 4,569,588 | 2/1986 | Nishiwaki et al. | 356/349 |
| 4,641,527 | 2/1987 | Hiroi et al. | 73/657 |

OTHER PUBLICATIONS

"Laser Doppler Vibration Measuring System Using Bispectral Analysis" by Osami Sasaki et al., Applied Optics, vol. 19, No. 1, Jan. 1980.

"A Laser Device for Remote Vibration Measurement" by John Foster, IEEE Trans. Aerospace & Electronic Systems, vol. AES-3, No. 2, Mar. '67.

*Primary Examiner*—Stewart J. Levy
*Assistant Examiner*—Louis M. Arana
*Attorney, Agent, or Firm*—Foley & Lardner, Schwartz, Jeffery, Schwaab, Mack, Blumenthal & Evans

[57] ABSTRACT

Measuring vibrational frequency of a pin attached at one end by collimating two laser beams onto the pin and back scattering the beams. The back scattered frequency is modulated by doppler effect and is heterodyned with the original beam frequency to produce a signal representative of each modulating frequency. The representative signals are summed together and also subtracted from one another. The summed and subtracted signals are representative, one of the vibrational frequency of the pin and the other of the degree of focussing accuracy of each laser beam onto the pin.

9 Claims, 1 Drawing Sheet

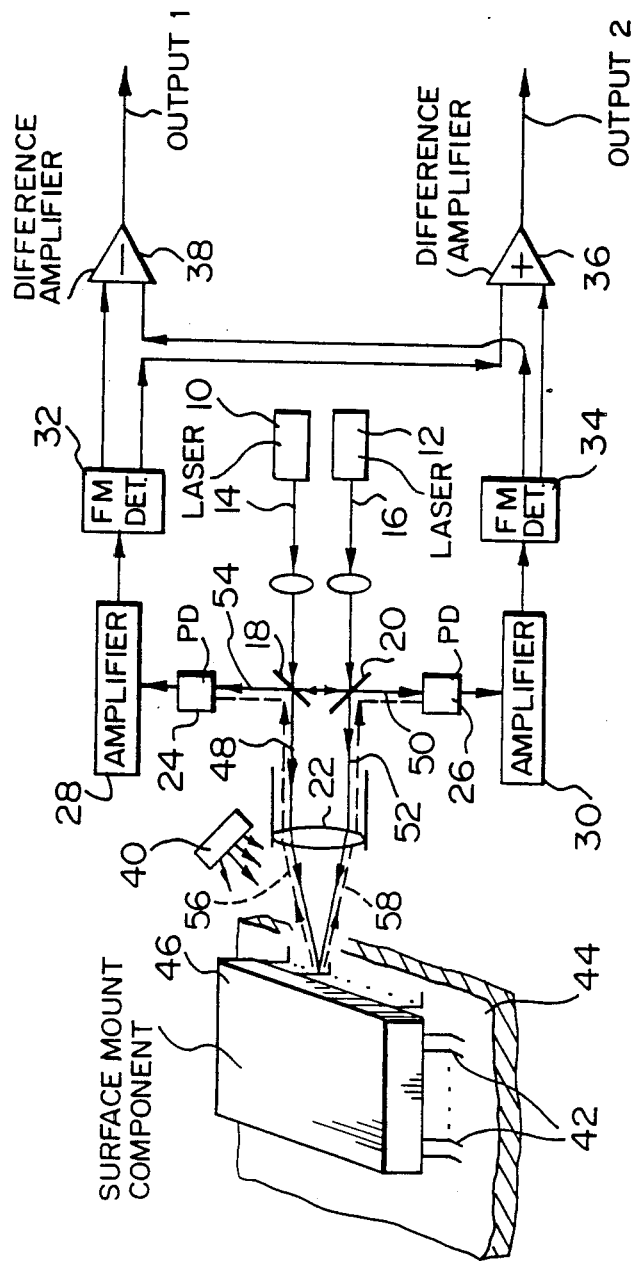

MEASURING VIBRATIONAL FREQUENCY OF VIBRATABLE PINS

This invention relates to the measuring of vibrational frequency of vibratable pins.

Electronics devices include members referred to as hybrids. A hybrid comprises a ceramic base carrying a resistor network and surface mounted components on the base. Some surface mounted components have conductor pins extending from bodies of the components and electrically connected to terminals of the resistor network. This electrical connection is produced by soldering the conductor pins to the terminals.

Because of the small size and closeness together of the conductor pins, it may be difficult to determine whether each conductor pin has been positively connected to its respective terminal during the soldering operation. Inspection procedures have been found to be unreliable particularly when they are performed visually. Visual inspection involves the use of skilled inspection personnel who need to consider every joint visually. This procedure is inordinately lengthy and quality control may be constantly a risk because of human error.

The present invention provides a method and apparatus which seeks to produce results indicative of whether or not a satisfactory positive joint has been made between a pin and a terminal of a resistor network in a hybrid.

Accordingly, the present invention provides a method for measuring the vibrational frequency of a vibratable pin attached by at least one end to a fixed object comprising: causing the pin to vibrate; collimating two laser beams, each of a certain frequency, onto the vibrating pin such that the vibrating pin causes each laser beam to back scatter with a frequency which is modulated by doppler effect from said certain frequency of the beam; heterodyning each certain frequency with the modulated frequencies and emitting signals representative of each modulating frequency; and effecting a summation of the representative signals and a subtraction one from the other of the representative signals, said summation and subtraction being representative, one of the vibrational frequency of the pin and the other of the degree of focusing accuracy of each laser beam onto the pin.

If the natural frequency of a pin which has been correctly soldered to a fixed object is known, then the summation and subtraction results will identify whether the vibrational frequency of the pin being tested is approximately that for the correctly soldered pin or alternatively is of a pin for which the solder joint is defective.

In the method according to the invention, it is preferable that the pin is caused to vibrate by directing energy at it from an acoustic waveguide transducer.

In a practical method, each laser beam is directed at an individual beam splitter to split the beam into two parts, one part to follow a path transmitted through the splitter and the other part to follow a path reflected by the splitter. The certain frequency of the reflected part of each laser beam is heterodyned with the modulated frequencies and a signal representative of each modulating frequency is emitted. Preferably, the heterodyning function for the two laser beams is provided by two photodetectors, the reflected part of each laser beam passing to an individual photodetector together with the back scattered beams at the modulated frequencies. Heterodyne signals are passed from each photodetector to an amplifier which produces an amplified signal representative of the difference between the frequency of the respective laser beam and the modulated frequency of the other beam. The amplified signal is received by an FM detector which emits a signal representative of each modulating frequency.

The frequencies of the two beams may be identical or different from one another.

The invention also includes apparatus for measuring the vibrational frequency of a vibratable pin attached by at least one end to a fixed object comprising: means for vibrating the pin; means for collimating light to produce two laser beams, each of certain frequency, and for directing the beams onto the pin during operation of the pin vibrating means such that the vibrating pin back scatters each laser beam with a frequency which is modulated by doppler effect from said certain frequency of the beam; means for heterodyning said certain frequencies with the modulated frequencies and to emit signals representative of each modulating frequency; and means for summing said representative signals together for producing a signal of summation and means for subtracting said representative signals from one another for producing a signal of subtraction, one of the signals of summation and subtraction being representative of the vibrational frequency of the pin and the other signal being indicative of the focusing accuracy of each of the laser beams onto the vibrating pin.

One embodiment of the invention will now be described, by way of example, with reference to the accompanying drawing which is a diagrammatic view of apparatus for measuring the vibrational frequency of a pin.

As shown in apparatus for measuring the vibrational frequency of a vibratable pin comprises means for collimating light to produce two laser beams. This means is in the form of two laser beam sources 10 and 12. The sources 10 and 12 respectively produce laser beams 14 and 16. The beam 14 has a frequency of f1 and the beam 16 has a frequency of f2. Means is also provided for directing each of the beams onto a vibrating pin as will be described, said directing means comprising two beam splitters 18 and 20, one for each of the beams 14 and 16, and a deflecting lens 22. Each beam splitter will reflect part of its beam and transmit another part of its beam through it. The deflecting lens 22 is positioned so that a transmitted part of each beam 14 and 16 passes through and is deflected by it so that the two transmitted parts are caused to converge together to focus upon a certain spatial position in which the vibrating pin to be tested will be located.

The apparatus also includes a means for heterodyning the frequencies of the two beams with their frequencies after they have been back scattered by reflection upon a vibrating pin and thus after these frequencies have been modulated by the doppler effect. In the case of each beam 14 and 16, the heterodyning means comprises a photodetector 24 and 26 and amplifier 28 and 30, each photodetector and amplifier being disposed in series so as to receive a reflected part of one of the beams. FM detectors 32 and 34 are disposed so as to receive certain signals, as will be described, from the amplifiers, one detector to each amplifier, and to emit signals representative of the modulating frequencies imposed upon the two beams 14 and 16 by the doppler effect. The two detectors 32 and 34 are suitably connected to a summing amplifier 36 and difference amplifier 38 in which the emitted signals are summed and subtracted from one another.

The apparatus is also provided with a means for vibrating a pin upon which the two beams 14 and 16 are to be directed. This vibrating means comprises an acoustic waveguide transducer 40 which is orientated to direct energy at the spatial position at which the transmitted parts of the beams 14 and 16 converge.

The apparatus described above is to be used for testing the vibrational frequency of each of the pins 42 which extend between a ceramic base 44 and a surface mounted component 46 of a hybrid. The ceramic base 44 also includes a resistor network the structure of which is not relevant to the present invention and therefore is not shown.

It is known that if each of the conductor pins 42 has been correctly soldered at its ends both to the base 44 and the surface mounted component 46, then each pin will vibrate when subjected to a vibrating force, at approximately the same known natural frequency. However, should one of the soldered joints be defective, i.e. broken, or not completed, on any pin, then that pin will vibrate at a frequency which is substantially different from the known natural frequency when correctly soldered. This substantial difference can be detected with the apparatus of the embodiment.

As shown in the FIGURE, the vibrational characteristics of the pins are tested in series by intermittently relatively moving the hybrid and the apparatus so that each pin, in turn, is disposed in the spatial position at which the beams 14 and 16 converge. For the testing of any one particular pin, the pin is caused to vibrate by the energy transmitted from the acoustic waveguide transducer 40 and, as the pin is vibrating, the two beams 14 and 16 are directed from their sources 10 and 12. The beam 14 is split into two parts by the beam splitter 18, namely a transmitted part 48 which proceeds through the deflector lens 22 and a reflected part 50 which passes downwardly as shown in the FIGURE and through the beam splitter 20 so as to be directed at the photodetector 26. Similarly, the laser beam 16 has a transmitted part 52 which passes through the beam deflector lens 22 and a reflected part 54 which is directed at the photodetector 24. The two transmitted parts 48 and 52 of the beams converge at their frequencies f1 and f2 upon the spatial position which is occupied by the conductor pin 42 under test. Upon impinging upon the conductor pin, each of the transmitted parts 48 and 52 of the beams 14 and 16 is reflected by being back scattered from the pin and its frequency is modulated by the doppler effect as caused by the pin vibration. As a result, the frequency of the beam 14 has a back scattered modulation of f1+fd1 while the frequency f2 of the beam 16 has a back scattered modulated frequency of f2+fd2.

Certain directed parts 56 and 58 of the back scattered modulated frequency beams pass through the deflector lens 22 so as to be reflected by the beam splitters 18 and 20 towards the two photodetectors 24 and 26. Thus, in addition to the photodetectors 24 and 26 receiving, respectively, the reflected parts 54 and 50 of beams 14 and 16 at frequencies f2 and f1, they both receive back scattered beams at the modulated frequencies. The frequencies are heterodyned in each of the photodetectors 24 and 26 and heterodyned signals are sent by each of the photodetectors to its respective amplifier 28 and 30.

Each amplifier is tuned so as to produce and transmit to its frequency modulating detector 32 or 34, an amplified signal which is representative of the difference between the frequency of its respective laser beam 14 or 16 and the modulated frequency of the other beam. It follows therefore that whereas photodetector 24 detects the frequencies: f2; f1+fd1; and f2+fd2, the amplified signal transmitted from amplifier 28 is representative of the heterodyned frequency f2−(f1+fd1). Similarly, the amplifier 30 transmits a signal to the frequency modulated detector 34 which is representative of the heterodyned signal (f2+fd2)−f1. These amplified signals are then received by the FM detectors 32 and 34.

The two FM detectors 32 and 34 are tuned so as to emit signals representative of each modulating frequency, i.e. fd1 and fd2. In effect, therefore, the detector 32 produces a signal representative of the frequency fd1 and the detector 34 a signal representative of the frequency fd2. These two signals are then passed to the difference and summing amplifiers 36 and 38. As may be seen from the above, the signal for frequency fd2 is positive whereas that of signal fd1 is negative. Hence the summing amplifier will give a minimum output whereas the difference amplifier will give a maximum output for the two signals. These outputs may be visually shown in conventional fashion upon an oscilloscope or digital readout.

The maximum output after averaging, corresponds to the actual doppler shift or frequency of the particular conductor pin under test. This result may easily be compared with the expected natural frequency of the pin if it has been soldered correctly so as to indicate whether or not the soldering of the particular pin is satisfactory.

The minimum output produced by the summing amplifier however will indicate the degree of accuracy of impingement of the beams 14 and 16 upon the pin. Pins being tested are substantially narrow and great care needs to be taken to ensure that the beams impinge properly upon each pin before correct readings concerning the vibrational characteristics can be relied upon. It follows that if the two beams are correctly aligned upon a pin under test, then the summing amplifier should give a minimum output result. Alternatively, if the result given by the summing amplifier is above the minimum, then this is an indication that one of the beams 14 and 16 at least overlaps an edge of the pin so that the back scattering characteristics are affected. As may be suspected, if such differing characteristics are achieved, then this may produce incorrect and varying results from the difference amplifier so that a correct reading as to the frequency of the vibrating pin cannot be achieved. However, should the summing amplifier produce the minimum output expected for correctly aligned beams upon the pin, then reliance can be placed upon the indicator frequencies from the difference amplifier being correct.

The above embodiment shows that the invention is both simple in structure and in operation. In addition, with the use of the two beams for vibration measurement, the modulating frequencies may be summed and subtracted to enable the positioning of the beams upon the pin to be checked during the whole of the testing procedure thereby eliminating any errors in alignment which may be present or occur during the use of the apparatus.

What is claimed is:

1. A method for measuring the vibrational frequency of a vibratable pin attached by at least one end to a fixed object comprising:
   causing the pin to vibrate;
   collimating two laser beams, each of a certain frequency, onto the vibrating pin such that the vibrating pin causes each laser beam to back scatter with a frequency which is modulated by doppler effect from said certain frequency of the beam;
   heterodyning each certain frequency with the modulated frequencies and emitting signals representative of each modulating frequency; and
   effecting a summation of the representative signals and a subtraction from one another of the representative signals, said summation and subtraction being representative, one of the vibrational frequency of the pin and the other of the degree of focusing accuracy of each laser beam onto the pin.

2. A method according to claim 1 comprising causing the pin to vibrate by directing energy from an acoustic waveguide transducer at the pin.

3. A method according to claim 1 comprising directing each laser beam at an individual beam splitter to split the beam into parts, a transmitted part to follow a path transmitted through the splitter to the pin, and a reflected part to follow a path reflected by the splitter; and heterodyning the certain frequency of the reflected part of each laser beam with the modulated frequencies and emitting signals representative of each modulating frequency.

4. A method according to claim 3 comprising passing the reflected part of each laser beam to an individual photodetector together with the back scattered beams at the modulated frequencies, heterodyning the frequencies in the photodetector, transmitting heterodyne signals from each photodetector to an amplifier, transmitting an amplified signal from each amplifier representative of the difference between the frequency of the respective laser beam and of the modulated frequency of the other beam, receiving said amplified signal in a frequency modulating detector, and emitting from each frequency modulating detector signals representative of each modulating frequency.

5. A method according to claim 3 wherein the two laser beams are produced with different frequencies.

6. A method according to claim 3 wherein the two laser beams are produced with the same frequency.

7. Apparatus for measuring the vibrational frequency of a vibratable pin attached by at least one end to a fixed object comprising:
   means for vibrating the pin;
   means for collimating light to produce two laser beams, each of certain frequency, and for directing the beams onto the pin during operation of the pin vibrating means such that the vibrating pin reflects each laser beam with a frequency which is modulated by doppler effect from said certain frequency of the beam;
   means for heterodyning said certain frequencies with the modulated frequencies and to emit signals representative of each modulating frequency; and
   means for summing said representative signals together for producing a signal of summation and means for subtracting said representative signals from one another for producing a signal of subtraction, one of the signals of summation and subtraction being representative of the vibrational frequency of the pin and the other signal being indicative of the focusing accuracy of each of the laser beams onto the vibrating pin.

8. Apparatus according to claim 7 wherein the means for directing each of the beams comprises an individual beam splitter to split the beam into two parts, a transmitted part to follow a path transmitted through the splitter and a reflected part to follow a path reflected by the splitter to the heterodyning means, and lens means to cause convergence of said transmitted parts of the two beams at the pin.

9. Apparatus according to claim 8 wherein the heterodyning means comprises two photodetectors, one for receiving the reflected part of each laser beam, and an amplifier associated with each photodetector for receiving heterodyne signals transmitted by each photodetector and for transmitting an amplified signal representative of the difference between the frequency of the respective laser beam and the modified frequency of the other laser beam, and a frequency modulating detector is provided for receiving amplified signals from each amplifier, each frequency modulating detector tuned to emit the signals representative of each modifying frequency.

* * * * *